United States Patent
Ponton

(10) Patent No.: US 7,930,013 B2
(45) Date of Patent: Apr. 19, 2011

(54) SENSOR ASSEMBLY WITH CONDUCTIVE BRIDGE

(75) Inventor: Curtis W. Ponton, El Paso, TX (US)

(73) Assignee: Compumedics Limited, Victoria (AU)

( * ) Notice: Subject to any disclaimer, the term of this patent is extended or adjusted under 35 U.S.C. 154(b) by 1266 days.

(21) Appl. No.: 11/478,014

(22) Filed: Jun. 29, 2006

(65) Prior Publication Data

US 2007/0004978 A1    Jan. 4, 2007

Related U.S. Application Data

(60) Provisional application No. 60/695,554, filed on Jun. 29, 2005.

(51) Int. Cl.
*A61B 5/0478* (2006.01)
(52) U.S. Cl. .......... 600/383; 600/393; 600/397
(58) Field of Classification Search .......... 600/372, 600/383, 393, 397
See application file for complete search history.

(56) References Cited

U.S. PATENT DOCUMENTS

| | | | |
|---|---|---|---|
| 3,508,541 A * | 4/1970 | Westbrook et al. | 600/383 |
| 3,659,614 A * | 5/1972 | Jankelson | 607/139 |
| 3,788,317 A * | 1/1974 | McCormick | 600/392 |
| 3,982,529 A | 9/1976 | Sato | |
| 4,166,457 A * | 9/1979 | Jacobsen et al. | 600/397 |
| 4,535,779 A | 8/1985 | Ober | |
| 5,348,006 A | 9/1994 | Tucker | |
| 6,067,464 A * | 5/2000 | Musha | 600/383 |
| 6,574,513 B1 | 6/2003 | Collura et al. | |
| 2002/0016538 A1 | 2/2002 | Gopinathan et al. | |

FOREIGN PATENT DOCUMENTS

| | | |
|---|---|---|
| EP | 1332771 A2 | 8/2003 |
| JP | 2005-161025 A | 6/2005 |

OTHER PUBLICATIONS

PCT/AU2006/000899 International Search Report, Sep. 7, 2006, Compumedics Limited.

* cited by examiner

*Primary Examiner* — Lee S Cohen
(74) *Attorney, Agent, or Firm* — Sughrue Mion, PLLC

(57) ABSTRACT

A sensor assembly for the measurement of electrophysiological signals and including a conductive bridge is provided. In one embodiment, the conductive bridge is provided by an expandable member with an absorbent material attached to one end. An aperture extends through the expandable member, forming a cavity well. Addition of a conductive medium to the cavity well allows the conductive bridge to provide a conductive pathway between an electrode and a patient's skin.

20 Claims, 6 Drawing Sheets

US 7,930,013 B2

SENSOR ASSEMBLY WITH CONDUCTIVE BRIDGE

RELATED APPLICATION

This application claims the benefit of U.S. Provisional Application No. 60/695,554, filed Jun. 29, 2005.

FIELD OF THE INVENTION

The invention relates generally to sensors for the measurement of electrophysiological signals, and more particularly an electrode assembly for monitoring electroencephalogram (EEG) signals.

BACKGROUND

When measuring a patient's electrophysiological signals, a conductive bridge is typically used between an electrode and the patient's skin in order to provide electrical communication between the skin and the electrode. Previously, most conductive bridges were simply gels or pastes placed between the electrode and skin. While this method generally works for its intended purpose, there are some disadvantages to the uses of gels and pastes. For example, air pockets may form in gels or pastes and these air pockets could affect the accuracy of the readings. Secondly, the gel or paste may dry after prolonged use, thus also affecting the recorded data. Thirdly, gels and pastes can be messy when applied, especially in cases such as EEG tests wherein the electrode is placed over thick hair.

SUMMARY OF INVENTION

The present invention is directed to a sensor assembly used in the monitoring of electrophysiological signals. The present invention is also directed to a conductive bridge that forms part of a sensor assembly. In one embodiment, the present invention is used to measure electroencephalogram (EEG) signals.

The conductive bridge may be placed between an electrode and a patient's skin. In one embodiment, the conductive bridge is an assembly comprised of an expandable member with an absorbent material attached to one end. An aperture extends through the expandable member, forming a cavity well. The addition of a conductive medium to the cavity well allows the conductive bridge to provide a conductive pathway for electrophysiological signals emanating from the patient. When a conductive medium is added to the cavity well, the medium is absorbed into the expandable member. The absorption of conductive medium causes the expandable member to expand vertically. When used with an EEG cap, this expansion develops moderate pressure to maintain the conductive bridge against the patient's skin.

The conductive bridge can be used as a substitute for or in addition to the conductive gel or paste that is often used when measuring electrophysiological signals. For example, it can be used in disk electrode-based EEG caps. Embodiments of the invention provide a low impedance sensor, thereby promoting accurate measurement of electrophysiological signals. Minimal impedance is desired as a reduced impedance allows the electrode to obtain a stronger and more accurate reading of electrophysiological signals.

Embodiments of the invention also promote easy clean-up for the test subject, when compared to gel or paste methods. Further, embodiments of the present invention are able to slowly dispense conductive media from a cavity well to the expandable member over time, thereby enabling consistent measurement of electrophysiological signals over a prolonged time period.

BRIEF DESCRIPTION OF THE DRAWINGS

For the purposes of facilitating the understanding of the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

DETAILED DESCRIPTION

For the purpose of explanation only, the subject invention is described with respect to an embodiment which is adapted for use in recording EEG signals. One skilled in the art can readily ascertain that the subject invention may be applicable for other uses wherein electrophysiological signals are taken.

The subject invention relates to an electrode assembly 10 comprised of a housing 30, an electrode 50, and a conductive bridge 40.

Figure 1:
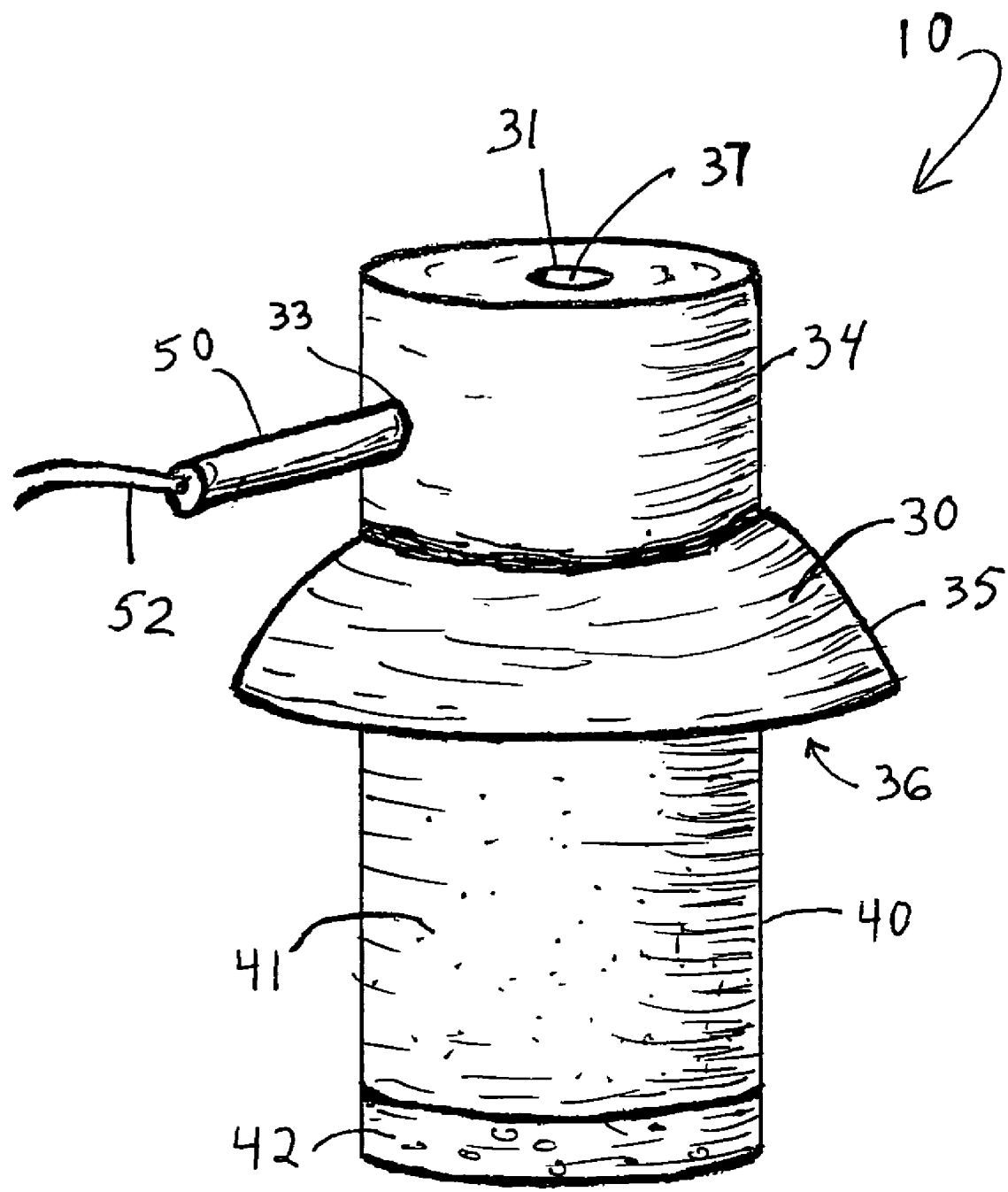
FIG. 1 is a view of one embodiment of a sensor assembly according to the present invention.
Figure 2:
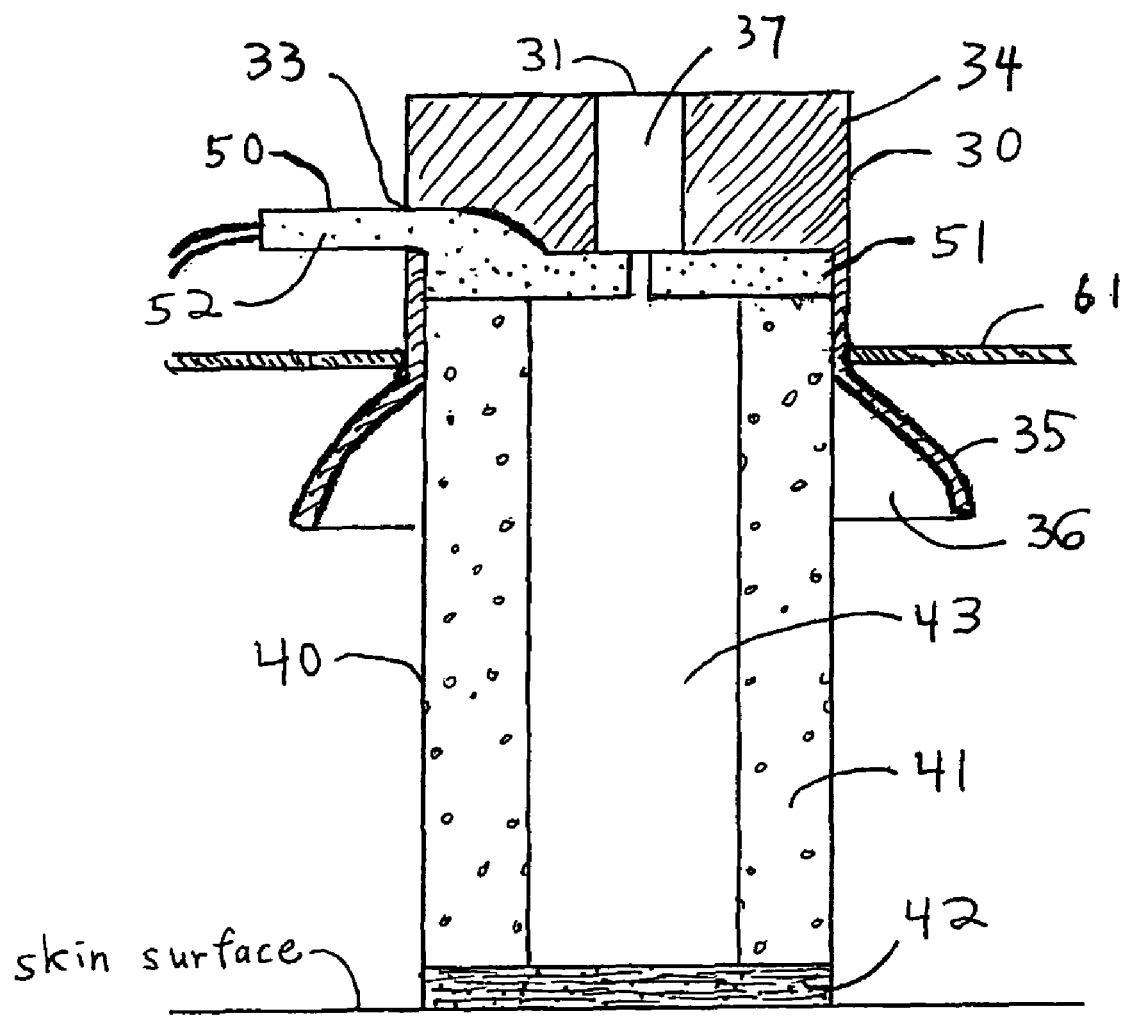
FIG. 2 is a cross sectional view of one embodiment of a sensor assembly according to the present invention.

As shown in FIG. 2, the subject invention also relates to a conductive bridge 40 placed between electrode 50 and a patient's skin in order to provide a conductive pathway for electrophysiological signals emanating from the patient. As shown in FIG. 1, in one embodiment, the subject conductive bridge 40 is a generally cylindrical (although other shapes may be used) assembly comprised of an expandable member 41 with an absorbent material 42 attached to one end. As shown in FIGS. 2 and 4, an aperture extends through expandable member 41 and together with the top surface of absorbent material 42 defines a well 43.

Figure 3:
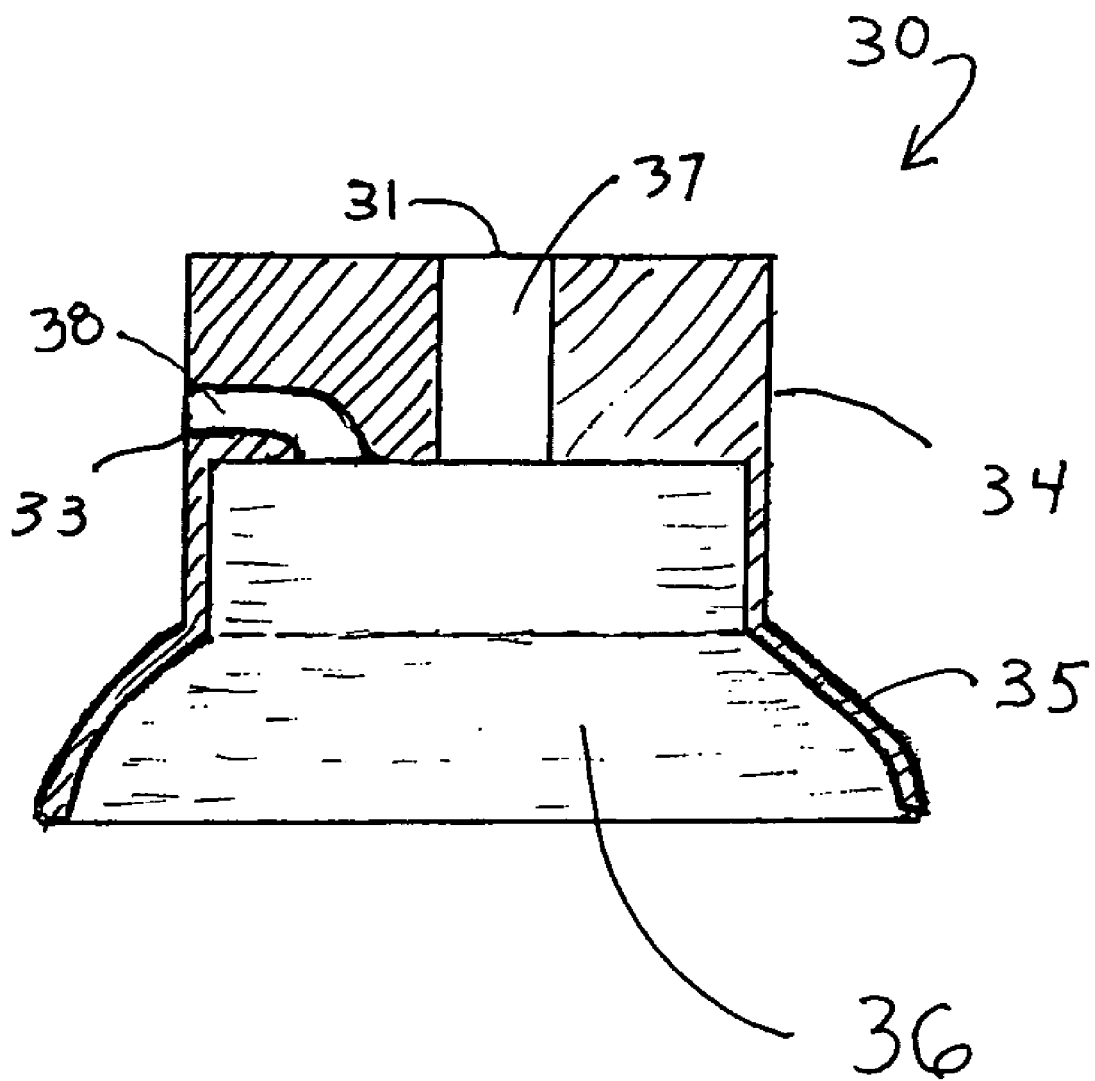
FIG. 3 is a cross sectional view of one embodiment of a housing suitable for use with a sensor assembly according to the present invention.

FIG. 3 is a cross sectional view of housing 30. Housing 30 defines a pair of apertures 31, 33, a generally cylindrical portion 34 and a portion 35 having a generally frusto-conical profile. Housing 30 is preferably manufactured of a resilient material. Housing 30 defines a cavity 36 into which a portion of expandable member 41 is received. Within portion 34, cavity 36 may have an internal diameter which is sized to frictionally hold expandable member 41 in place. Aperture 31 opens into a passageway 37 and aperture 33 opens into a passageway 38 through which a portion of electrode 50 is received. As described in more detail herein, passageway 37 provides a liquid path for a conductive medium.

Figure 4A:
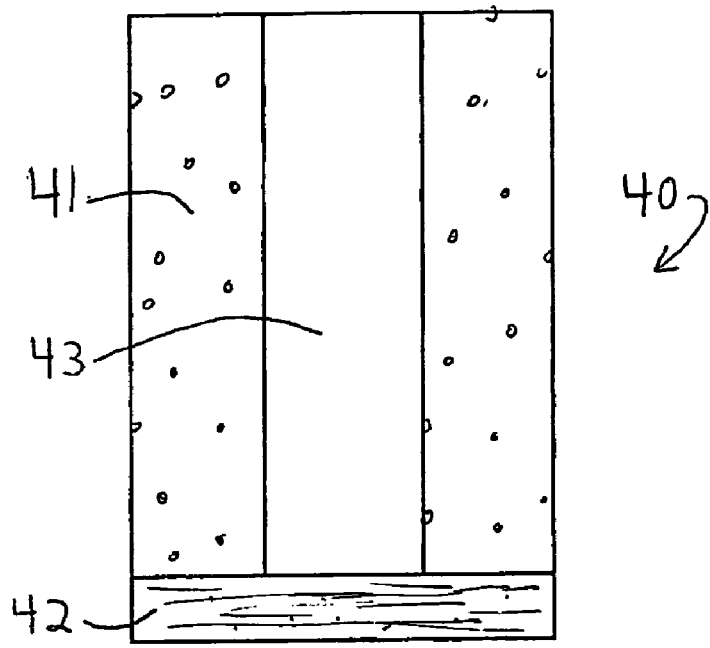
FIG. 4A is a cross sectional view of one embodiment of an expandable member according to one embodiment of the present invention.
Figure 4B:
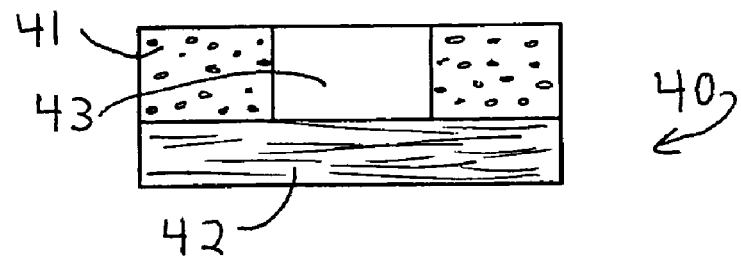
FIG. 4B is a cross sectional view of the expandable member of FIG. 4a when in a dry, compressed state.

Referring now to FIG. 4, conductive bridge 40 includes expandable member 41 and absorbent material 42. Expandable member 41 may initially be provided in a dry, compressed state, as indicated in FIG. 4B. Upon absorption of a conductive medium, including but not limited to an aqueous solution, ionic solution or salt solution, expandable member 41 expands vertically into an expanded state, as indicated in FIG. 4A. Expandable member 41 may be manufactured of a variety of different materials including, but not limited to, materials such as synthetic sponge, cellulose, foam and reticulated polymers of polyurethane, etc. Other materials for expandable member 41 suitable for use in the present invention may be apparent to those of ordinary skill in the art. For example, materials forming a three-dimensional reticulated matrix of cells may be suitable for use in the present invention. When removed from housing 30 and after application of a conductive medium, expandable member 41 absorbs conductive medium and expands in thickness (height dimension in FIG. 4) from 50% to 1000% of its initial dry height. More preferably, expandable member 41 expands from 100% to 500% of its initial dry height upon application of the conductive medium.

Absorbent material 42 defines the bottom surface of well 43. In operation, absorbent material 42 also defines an engaging surface for contacting a patient's scalp. Preferably, absorbent material 42 should serve to provide an even distribution of the conductive medium to the scalp. Absorbent material 42 may be manufactured of a variety of different materials including, but not limited to, fabric materials such as felts, or other fabric of matted, compressed fibers. Other materials for absorbent material 42 suitable for use in the present invention may be apparent to those of ordinary skill in the art.

In one embodiment, as illustrated in FIG. 4, expandable member 41 is a sponge material which is dry and compressed to about 1.8 to 2.5 mm in height. Fully expanded (hydrated), the expandable member 41 can reach up to 18 mm in height. In a typical application, the expandable member 41 assumes a height of between 5 mm to 8 mm. The expandable member 41 and the absorbent material 42 have a diameter of about 6.35 mm. An aperture extends through the center of the expandable member 41, forming well 43 which has a diameter of approximately 3.2 mm. In one embodiment, absorbent material 42 is a generally cylindrical felt layer having a thickness of approximately 1.25 mm. Absorbent material 42 is adhered to the expandable member 41 on one end and forms the bottom of well 43. Approaches to securing the absorbent material 42 to the expandable member 41 may also be practicable including, but not limited to, other thermal, chemical, and/or mechanical bonding technologies.

Figure 5:
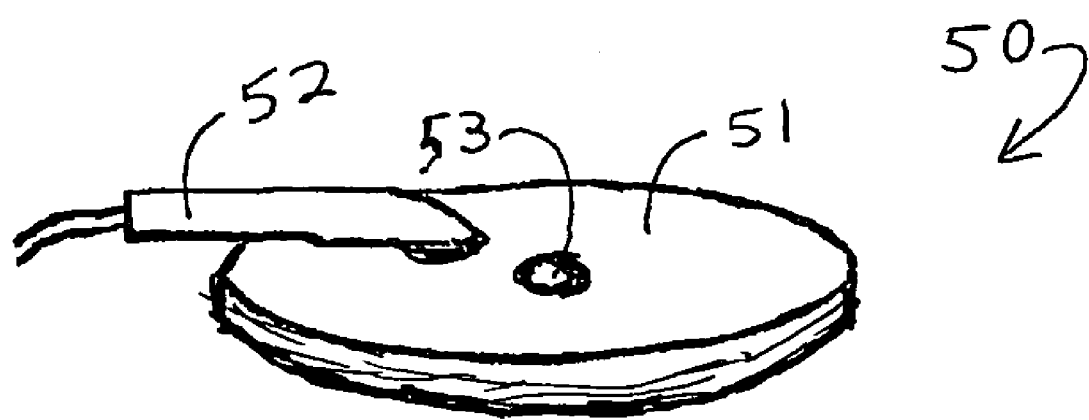
FIG. 5 is a view of one embodiment of an electrode suitable for use with a sensor assembly according to the present invention.
Figure 6:
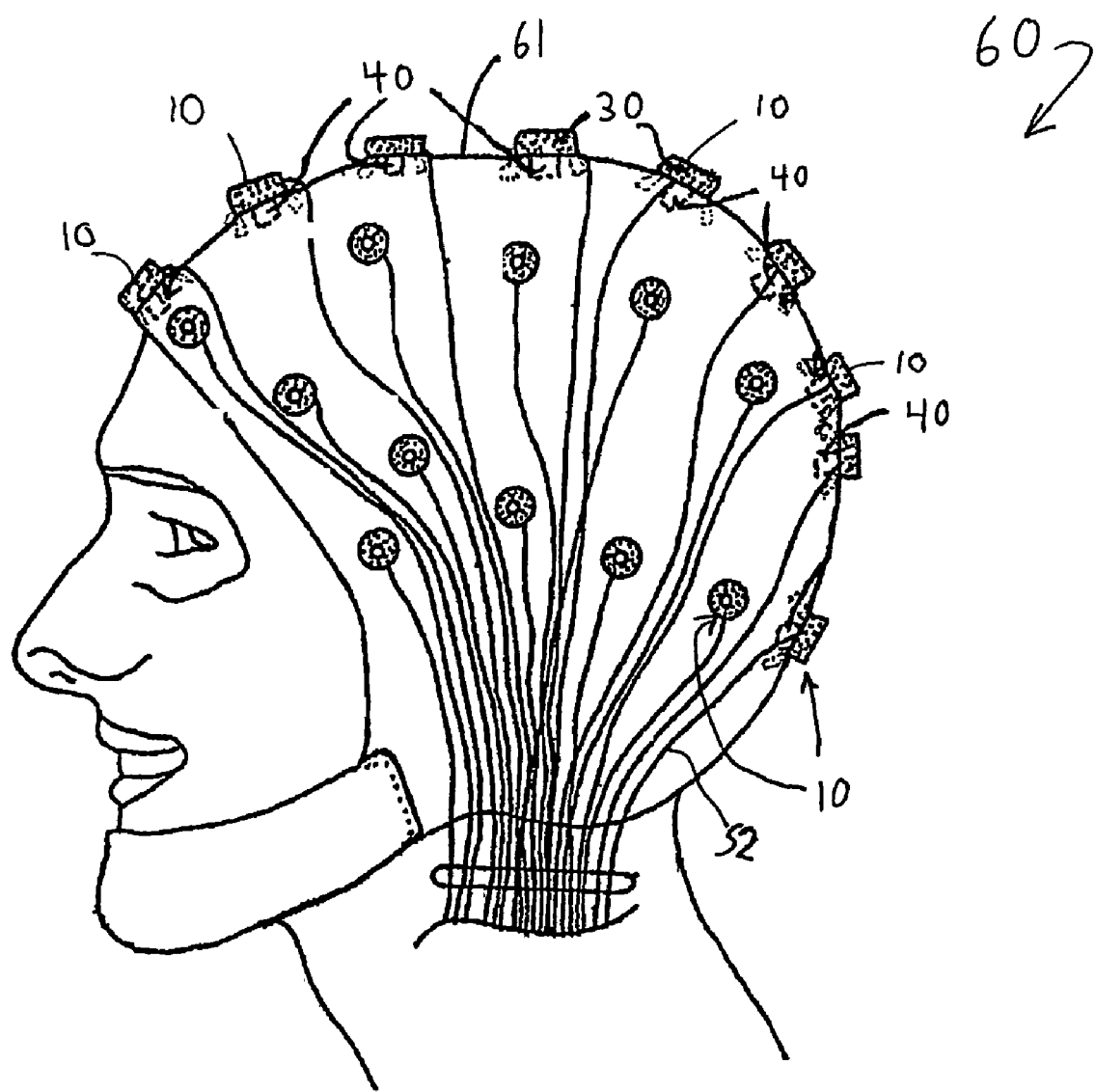
FIG. 6 is a side view of one embodiment of an EEG cap having a plurality of sensor assemblies according to the present invention.

In one embodiment, as used in the measurement of EEG signals, conductive bridge 40 is placed in its compressed state between disk electrode 50 (shown in FIG. 5) and a patient's scalp. Disk electrode 50 includes a disk portion 51 and an electrode lead 52. An aperture 53 extends through disk portion 51. As shown in FIG. 2, each disk electrode 50 is typically held in place by housing 30 (shown in FIG. 3). As shown in FIG. 6, a plurality of housings 30 can be held by a flexible surface 61 of an EEG cap 60. In cooperation, the disk electrode 50, housing 30, and EEG cap 60 retain conductive bridge 40 in place.

In one embodiment, a conductive medium is applied to well 43 after the EEG cap 60 is placed on the patient. The conductive medium is added, for example via a syringe, through aperture 31 and passageway 37 of electrode housing 30, and through aperture 53 of disk portion 51 of disk electrode 50. (See FIG. 2). The addition of a conductive medium to the well 43 causes the expandable member 41 to expand. Any portion of the medium that is not absorbed by the expandable member 41 is retained in the well 43 for subsequent release during use. In this manner, well 43 releases a conductive medium that will slowly dispense with time which allows for longer EEG recording sessions. As expandable member 41 expands in reaction to the applied conductive medium, conductive bridge 40 is retained in place by the disk electrode 50, housing 30, and EEG cap 60, creating contact pressure between the scalp and conductive bridge 40. Preferably absorbent material 42 engages the patient's scalp. As a result of the contact pressure created, the subject invention eliminates the need for abrading the patient's scalp, while still achieving low impedance. Rather than abrading the patient's scalp prior to placing the EEG cap on the patient, the patient can exfoliate his or her scalp using a bristle-type hair brush.

Preferably, the conductive medium is a conductive liquid solution (such as saline); however, other forms of conductive media such as low viscosity electrode gels can also be used. One example of a conductive electrolyte that can be used is formed from a combination of calcium chloride, potassium chloride, and baby shampoo. In combination with a conductive medium, the subject invention is able to achieve low impedances (less than about 10 kOhms) for more accurate monitoring of EEG signals. In preferred embodiments, the subject invention is able to achieve impedances of about 5 kOhms or less. Impedances can be decreased by providing a large contact surface between the conductive bridge and the electrode.

Once in place, conductive bridge 40 is able to slowly dispense conductive media from well 43 over time, enabling consistent EEG recording results over a prolonged period of time. Furthermore, it is also contemplated that conductive media can be delivered automatically to the sensor assembly 10 such as via a computer-controlled calibrated pipette system. For example, well 43 of the conductive bridge 40 can be refilled periodically without the need to remove the EEG cap 60 from the patient. This enables the EEG cap 60 to be used for even more prolonged periods of time.

It is also believed that embodiments of the subject invention can be manufactured at such minimal cost that it can be used as a one-time use disposable product. Consequently, after each EEG session, the entire assembly (cap, conductive bridge and electrodes) can be disposed. One-time use of the assembly eliminates the risk of patient-to-patient cross contamination.

Preferred embodiments of the subject invention are compatible with existing electrode caps, such as caps containing electrodes with flat disk surfaces. For instance, a preferred embodiment can be used with Compumedics Neuroscan Amplifiers such as the SynAmp2. The conductive medium used with the subject invention may then be delivered to each electrode location in the electrode cap, through the existing entrance points for the blunt needles previously used to deliver gels to the electrode locations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification or shown in the drawings. As one of ordinary skill in the art will readily appreciate from the disclosure of the present invention, the processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Any numbering or ordering of elements in the following claims is merely for convenience and is not intended to suggest that the ordering of the elements of the claims has any particular significance.

What is claimed is:

1. A sensor assembly comprising:
   a housing;
   an electrode held by said housing;
   an expandable member received within at least a portion of the housing, and providing a conductive pathway for physiologic signals, wherein an aperture extends through said expandable member between a first end and a second end, and wherein the second end is connected with the electrode; and
   an absorbent material, wherein said absorbent material is connected to said first end of the expandable member, such that said expandable member and said absorbent material cooperate to define a well for receiving a conductive medium.

2. The sensor assembly of claim 1, wherein the expandable member is comprised of a sponge material.

3. The sensor assembly of claim 1, wherein the expandable member is comprised of cellulose.

4. The sensor assembly of claim 1, wherein the absorbent material is comprised of a fabric.

5. The sensor assembly of claim 1, wherein the absorbent material is comprised of felt.

6. The sensor assembly of claim 1, wherein the sensor assembly is adapted for use with an electroencephalogram cap.

7. The sensor assembly of claim 1, further comprising: a conductive medium absorbed into the expandable member.

8. The sensor assembly of claim 7 adapted to achieve an impedance of less than about 10 kOhms after said expandable member absorbs said conductive medium in use.

9. The sensor assembly of claim 1, wherein a cylindrical cavity of said housing is in contact with portions of said expandable member.

10. The sensor assembly of claim 1, wherein said electrode is in contact with the expandable member.

11. The sensor assembly of claim 1, wherein said expandable member expands from about 50% to 1000% of its initial thickness upon application of said conductive medium.

12. The sensor assembly of claim 11, wherein said expandable member expands from about 100% to 500% of its initial thickness upon application of said conductive medium.

13. The sensor assembly of claim 1, wherein the absorbent material defines an engaging surface contacting a patient's scalp.

14. The sensor assembly of claim 1, wherein the expandable member, absorbent material and electrode cooperate to define the well.

15. An electroencephalogram cap, comprising a plurality of the sensor assemblies of claim 1.

16. A method comprising:
   providing an electrode assembly including an electrode, a housing adapted to retain said electrode, said housing defining a cavity in communication with a passageway, and an expandable member at least partially received into said cavity, wherein an aperture extends through said expandable member between a first end and a second end, and wherein the second end is connected with the electrode; and
   applying a conductive medium to said expandable member through said passageway, said applying including retaining a portion of said conductive medium within a well defined within the cavity, and said applying causing at least a portion of said expandable member to pass out of said cavity so as to maintain contact between said electrode assembly and a skin surface during data acquisition.

17. The method of claim 16 wherein said cavity is generally cylindrical and said expandable member includes a portion which is generally cylindrical.

18. A method of manufacturing a sensor, comprising the steps of:
   securing an expandable member to an absorbent material;
   placing an electrode into a housing;
   placing said expandable member within at least a portion of said housing such that a first end of the expandable member is in contact with the absorbent material and a second end of the expandable member is in contact with the electrode; and
   forming a hole within the expandable member, such that said expandable member and the absorbent material define a well for receiving a conductive medium.

19. A method of measuring electrophysiological signals, comprising the steps of:
   placing an electrode into a housing;
   inserting an expandable member into at least a portion of said housing, the expandable member providing a conductive pathway for physiologic signals, wherein an aperture extends through said expandable member between a first end and a second end, and wherein an absorbent material is connected to said first end of the expandable member such that said expandable member and said absorbent material cooperate to define a well for receiving a conductive medium;
   placing the absorbent material in contact with a patient's signal emanating surface; and,
   processing electrical signals sensed by the electrode and communicated through said absorbent material and said expandable member.

20. The method of claim 19, wherein upon said application of said conductive medium, said expandable member expands in thickness from about 50% to 500% of its original thickness.

* * * * *